US009101625B2

(12) United States Patent
Oksche et al.

(10) Patent No.: US 9,101,625 B2
(45) Date of Patent: Aug. 11, 2015

(54) BUPRENORPHINE-WAFER FOR DRUG SUBSTITUTION THERAPY

(75) Inventors: Alexander Oksche, Limburg (DE); William Heath, Cottenham (GB); Timothy Holden, Haddenham (GB); Derek A. Prater, Cambridge (GB); Richard S. Sackler, Greenwich, CT (US); Malcolm Walden, Cambs (GB)

(73) Assignee: PURDUE PHARMA L.P., Stamford, CT (US)

( * ) Notice: Subject to any disclaimer, the term of this patent is extended or adjusted under 35 U.S.C. 154(b) by 407 days.

(21) Appl. No.: 12/439,410

(22) PCT Filed: Aug. 29, 2007

(86) PCT No.: PCT/EP2007/058978
§ 371 (c)(1),
(2), (4) Date: Nov. 9, 2009

(87) PCT Pub. No.: WO2008/025791
PCT Pub. Date: Mar. 6, 2008

(65) Prior Publication Data
US 2010/0087470 A1 Apr. 8, 2010

(30) Foreign Application Priority Data
Aug. 30, 2006 (EP) .................. 06119839

(51) Int. Cl.
A61K 31/44 (2006.01)
A61K 31/485 (2006.01)
A61K 9/00 (2006.01)

(52) U.S. Cl.
CPC ............ A61K 31/485 (2013.01); A61K 9/006 (2013.01); A61K 9/0056 (2013.01)

(58) Field of Classification Search
None
See application file for complete search history.

(56) References Cited

U.S. PATENT DOCUMENTS

| | | |
|---|---|---|
| 3,773,955 A | 11/1973 | Pachter et al. |
| 3,966,940 A | 6/1976 | Pachter et al. |
| 4,070,494 A | 1/1978 | Hoffmeister et al. |
| 4,160,020 A | 7/1979 | Ayer et al. |
| 4,366,310 A | 12/1982 | Leslie |
| 4,464,378 A | 8/1984 | Hussain |
| 4,582,835 A | 4/1986 | Lewis et al. |
| 4,661,492 A | 4/1987 | Lewis et al. |
| 4,673,679 A * | 6/1987 | Aungst et al. .......... 514/282 |
| 4,764,378 A | 8/1988 | Keith et al. |
| 4,769,372 A | 9/1988 | Kreek |
| 4,882,335 A | 11/1989 | Sinclair |
| 4,889,860 A | 12/1989 | Rzeszotarski et al. |
| 4,935,428 A | 6/1990 | Lewis |
| 5,075,341 A | 12/1991 | Mendelson et al. |
| 5,079,018 A | 1/1992 | Ecanow |
| 5,149,538 A | 9/1992 | Granger et al. |
| 5,236,714 A | 8/1993 | Lee et al. |
| 5,298,261 A | 3/1994 | Pebley et al. |
| 5,426,112 A | 6/1995 | Zagon et al. |
| 5,466,464 A | 11/1995 | Masaki et al. |
| 5,472,943 A | 12/1995 | Crain et al. |
| 5,512,578 A | 4/1996 | Crain et al. |
| 5,556,838 A | 9/1996 | Mayer et al. |
| 5,580,876 A | 12/1996 | Crain et al. |
| 5,624,932 A | 4/1997 | Qin et al. |
| 5,629,003 A | 5/1997 | Horstmann et al. |
| 5,633,259 A | 5/1997 | Qin et al. |
| 5,767,125 A | 6/1998 | Crain et al. |
| 5,834,477 A | 11/1998 | Mioduszewski |
| 5,866,164 A | 2/1999 | Kuczynski et al. |
| 5,869,098 A | 2/1999 | Misra et al. |
| 5,958,459 A | 9/1999 | Chasin et al. |
| 5,968,547 A | 10/1999 | Reder et al. |
| 5,968,551 A | 10/1999 | Oshlack et al. |
| 6,048,541 A | 4/2000 | Misra et al. |
| 6,096,756 A | 8/2000 | Crain et al. |
| 6,228,863 B1 | 5/2001 | Palermo et al. |
| 6,277,384 B1 | 8/2001 | Kaiko et al. |
| 6,362,194 B1 | 3/2002 | Crain et al. |
| 6,375,957 B1 | 4/2002 | Kaiko et al. |
| 6,475,494 B2 | 11/2002 | Kaiko et al. |
| 6,627,635 B2 | 9/2003 | Palermo et al. |
| 6,680,071 B1 | 1/2004 | Johnson et al. |
| 6,696,066 B2 | 2/2004 | Kaiko et al. |
| 6,696,088 B2 | 2/2004 | Oshlack et al. |
| 6,716,449 B2 | 4/2004 | Oshlack et al. |
| 6,995,169 B2 | 2/2006 | Chapleo et al. |
| 7,144,587 B2 | 12/2006 | Oshlack et al. |

(Continued)

FOREIGN PATENT DOCUMENTS

AU 2002305559 B2 11/2002
CA 2 478 523 A1 10/2003

(Continued)

OTHER PUBLICATIONS

Strain et al (Drug and Alcohol Dependence 74:37-43, 2004).*
Leaflet entitled 'Ondansetron RL™ Zydis® Wafers' (Apr. 8, 2005).*
SUBOXONE Package Insert (available online as of at least Jul. 27, 2006 as evidenced by the attached Internet Archive Report).*
Internet Archive Report (accessed online Oct. 9, 2014).*
PVP Polyvinylpyrrolidone Polymers (accessed online Oct. 9, 2014).*
Karch's Pathology of Drug Abuse, Fourth Edition (2009, p. 436).*
"Australian Public Assessment Report for Buprenorphine/Naloxone—Propriety Product Name: Suboxone Sublingual Film—Sponsor: Reckitt Benckiser (Australia) Pty Ltd," PM-2009-01902-3-1, Commonwealth of Australia, 72 pages, Australia (Mar. 2011).

(Continued)

Primary Examiner — Craig Ricci
(74) Attorney, Agent, or Firm — Sterne, Kessler, Goldstein & Fox PLLC

(57) ABSTRACT

The present invention relates to oral pharmaceutical dosage forms comprising buprenorphine with the dosage form releasing buprenorphine instantly upon oral, preferably sublingual, application of the dosage form. The present invention also relates to the use of such dosage forms for treating pain in a human or animal or for drug substitution therapy in drug-dependent human subjects.

14 Claims, No Drawings

(56) References Cited

U.S. PATENT DOCUMENTS

| | | |
|---|---|---|
| 7,172,767 B2 | 2/2007 | Kaiko et al. |
| 7,201,920 B2 | 4/2007 | Kumar et al. |
| 7,332,182 B2 | 2/2008 | Sackler |
| 7,357,891 B2 | 4/2008 | Yang et al. |
| 7,419,686 B2 | 9/2008 | Kaiko et al. |
| 7,425,292 B2 | 9/2008 | Yang et al. |
| 7,749,542 B2 | 7/2010 | Kaiko et al. |
| 8,017,148 B2 | 9/2011 | Sackler |
| 8,017,150 B2 | 9/2011 | Yang et al. |
| 8,105,631 B2 | 1/2012 | Kaiko et al. |
| 8,475,832 B2 | 7/2013 | Myers et al. |
| 8,603,514 B2 | 12/2013 | Yang et al. |
| 8,932,630 B1 | 1/2015 | Kaiko et al. |
| 8,936,808 B1 | 1/2015 | Kaiko et al. |
| 2001/0051186 A1 | 12/2001 | Acharya et al. |
| 2002/0010127 A1 | 1/2002 | Oshlack et al. |
| 2003/0044458 A1 | 3/2003 | Wright, IV et al. |
| 2003/0059471 A1 | 3/2003 | Compton et al. |
| 2003/0065002 A1 | 4/2003 | Caruso et al. |
| 2003/0068371 A1 | 4/2003 | Oshlack et al. |
| 2003/0069263 A1 | 4/2003 | Breder et al. |
| 2003/0073714 A1 | 4/2003 | Breder et al. |
| 2003/0096012 A1 | 5/2003 | Besse et al. |
| 2003/0124185 A1 | 7/2003 | Oshlack et al. |
| 2003/0191147 A1 | 10/2003 | Sherman et al. |
| 2004/0092542 A1 | 5/2004 | Oshlack et al. |
| 2004/0176402 A1 | 9/2004 | Oshlack et al. |
| 2005/0085440 A1 | 4/2005 | Birch et al. |
| 2005/0112067 A1 | 5/2005 | Kumar et al. |
| 2005/0163830 A1 | 7/2005 | Rademacher et al. |
| 2005/0245483 A1 | 11/2005 | Brogmann et al. |
| 2006/0182801 A1 | 8/2006 | Breder et al. |
| 2007/0148097 A1* | 6/2007 | Finn et al. ............ 424/10.2 |
| 2007/0264327 A1 | 11/2007 | Kumar et al. |
| 2009/0291123 A1 | 11/2009 | Hoffmann et al. |
| 2015/0005331 A1 | 1/2015 | Wright et al. |

FOREIGN PATENT DOCUMENTS

| | | | |
|---|---|---|---|
| CA | 2 274 910 C | | 7/2005 |
| DE | 27 46 414 A1 | | 4/1979 |
| DE | 196 52 188 A1 | | 6/1998 |
| EP | 185 472 A1 | | 6/1986 |
| EP | 0 205 282 A2 | | 12/1986 |
| EP | 0 319 243 A1 | | 6/1989 |
| EP | 0 460 588 | | 12/1991 |
| EP | 0 651 997 A1 | | 12/1992 |
| EP | 1 260 216 A1 | | 11/2002 |
| GB | 1390772 | | 4/1975 |
| GB | 1 548 022 | | 7/1979 |
| GB | 1 548 022 A | | 7/1979 |
| GB | 2 328 443 A | | 2/1999 |
| JP | 08-291070 A | | 11/1996 |
| WO | WO 91/04757 | | 4/1991 |
| WO | WO 9602251 A1 | | 2/1996 |
| WO | WO 96/26720 A1 | | 9/1996 |
| WO | WO 97/06786 | | 2/1997 |
| WO | WO 97/33566 | | 9/1997 |
| WO | WO 98/26780 | * 11/1997 | ........... A62K 31/485 |
| WO | WO 98/26780 A2 | | 6/1998 |
| WO | WO 99/08658 A1 | | 2/1999 |
| WO | WO 99/09962 A1 | | 3/1999 |
| WO | WO 99/17744 A1 | | 4/1999 |
| WO | WO 99/32119 | | 7/1999 |
| WO | WO 99/32120 | | 7/1999 |
| WO | WO 99/44580 A1 | | 9/1999 |
| WO | WO 00/09171 A1 | | 2/2000 |
| WO | WO 00/16750 | | 3/2000 |
| WO | WO 00/23079 | | 4/2000 |
| WO | WO 00/51539 | | 9/2000 |
| WO | WO 00/51593 | | 9/2000 |
| WO | WO 00/59423 A1 | | 10/2000 |
| WO | WO 00/67739 | | 11/2000 |
| WO | WO 02/06373 A1 | | 1/2002 |
| WO | WO 03/003957 A1 | | 1/2003 |
| WO | WO 03/013433 A2 | | 2/2003 |
| WO | WO 03/015748 A2 | | 2/2003 |
| WO | WO 03/030883 A1 | | 4/2003 |
| WO | WO 03/070227 A1 | | 8/2003 |
| WO | WO 2005/004989 A2 | | 1/2005 |
| WO | WO 2005/053587 A1 | | 6/2005 |
| WO | WO 2005/079750 A2 | | 9/2005 |
| WO | WO 2006/087160 A1 | | 8/2006 |
| WO | WO 2007/070632 A2 | | 6/2007 |
| WO | WO 2007/088489 A2 | | 8/2007 |
| WO | WO 2007/093305 A2 | | 8/2007 |
| WO | WO 2007/144085 A1 | | 12/2007 |
| WO | WO 2008/025791 A1 | | 3/2008 |
| WO | WO 2008/040534 A2 | | 4/2008 |

OTHER PUBLICATIONS

English language Abstract of Japanese Patent Publication No. 08-291070, Japanese Patent Office, Patent Abstract of Japan (1996).

English language translation (unverified, machine generated) of German Patent Publication No. 27 46 414, European Patent Office, espacenet database—Worldwide, (2012).

International Search Report for International Application No. PCT/EP2007/058978, European Patent Office, Netherlands, mailed on Oct. 5, 2007.

RB Pharmaceuticals Limited, "Package Leaflet: Information for the User—Subutex 0.4 mg, 2 mg and 8 mg Sublingual Tablets—Buprenorphine hydrochloride," 5 pages, Reckitt Benckiser Healthcare (Sep. 2010).

Strain, E. C., et al., "Relative bioavailability of different buprenorphine formulations under chronic closing conditions," *Drug Alcohol Depend* 74(1):37-43, Elsevier Ireland Ltd., Ireland (Apr. 2004).

Co-pending U.S. Appl. No. 14/500,409, inventors Oksche, A. et al., filed Sep. 29, 2014.

Alvarez-Fuentes, J., et al., "Effectiveness of repeated administration of a new oral naltrexone controlled-release system on morphine analgesia," *J Pharm Pharmacol* 53:1201-1205, Pharmaceutical Society of Great Britain, England (2001).

Alvarez-Fuentes, J., et al., "Preclinical Study of an Oral Controlled Release Naltrexone Complex in Mice," *J Pharm Pharmacol* 52:659-663, Pharmaceutical Society of Great Britain, England (2000).

Amass, L., et al., "Efficacy of daily and alternate-day dosing regimens with the combination buprenorphine-naloxone tablet," *Drug and Alcohol Dependence* 58:143-152, Elsevier Science Ireland Ltd., Ireland (2000).

Archer, S., "Historical Perspective on the Chemistry and Development of Naltrexone," *NIDA Res Monogr* 28:3-10, National Institute on Drug Abuse, United States (1981).

Bashaw, E.D., et al., "Relative bioavailability of controlled-release oral morphine sulfate during naltrexone blockade," *Int J Clin Pharmacol Ther* 33(9):524-529, Dustri-Verlag Dr. K. Feistle, Germany (1995).

Bals-Kubik, R., et al., "Evidence that the aversive effects of opioid antagonists and κ-agonists are centrally mediated," *Phychopharmacology* 98:203-206, Springer-Verlag, Germany (1989).

Bigelow, G.E., et al., "Abuse Liability Assessment of Buprenorphine-Naloxone Combinations," Department of Psychiatry and Behavioral Sciences, The Johns Hopkins University School of Medicine.

Bloom, W.A., et al., "Clinical Studies with Naloxone/Methadone in a Ratio of 1:20," 5th National Conference on Methadone Treatment, Mar. 17-19, 1973, vol. Two: pp. 811 to 1504, 9 pages.

Co-pending U.S. Appl. No. 14/470,662 (Unpublished).

Caruso, F.S., et al., "Methadone and Naloxone in Combination (Naldone) for the Treatment of Heroin Addicts," *Proc Natl Conf Methadone Treat* 2:1336-1341, National Association for the Prevention of Addiction to Narcotics, United States (1973).

Cherny, N.I., "Opioid Analgesics Comparative Features and Prescribing Guidelines," *Drugs* 51(5):713-737, Adis International United, New Zealand (1996).

Chiang, C.N., et al., "Pharmacokinetics of the combination tablet of buprenorphine and naloxone," *Drug and Alcohol Dependence* 70:S39-S47, Elsevier Science Ireland Ltd., Ireland (2003).

(56) References Cited

OTHER PUBLICATIONS

Chiange, C.N., et al., "Kinetics of a naltrexone sustained-release preparation," Clinical pharmacology and therapeutics 35:704-708, Wiley, United States (1984).

Chiange, C.N., et al., "Clinical Evaluation of a Naltrexone Sustained-Release Preparation," *Drug and Alcohol Dependence* 16:1-8, Elsevier Scientific Publishers Ireland Ltd., Ireland (1985).

Ciccocioppo, R., et al., "Effect of nociceptin/orphanin FQ on the rewarding properties of morphine," *European Journal of Pharmacology* 404:153-159, Elsevier Science B.V., Netherlands (2000).

Comer, S.D., et al., "Depot naltrexone: long-lasting antagonism of the effects of heroin in humans," *Psychopharmacology* 159:351-360, Springer-Verlag, Germany (2002).

Crabtree, B.L., "Review of naltrexone, a long-acting opiate antagonist," *Clinical Pharmacy* 3:273-280, American Society of Hospital Pharmacists, United States (1984).

Crain, S.M., et al., "Antagonists of excitatory opioid receptor functions enhance morphine's analgesic potency and attenuate opioid tolerance/dependence liability," *Pain* 82:1-11, Elsevier Science B.V., Netherland (1999).

Crain, S.M., et al., "Ultra-low concentrations of naloxone selectively antagonize excitatory effect of morphine on sensory neurons, thereby increasing its antinociceptive potency and attenuating tolerance/dependence during chronic cotreatment," *Proc Natl Acad Sci USA* 92:10540-10544, United States National Academy of Sciences (1995).

Crain, S.M. and Shen, K-F., "Acute thermal hyperalgesia elicited by low-dose morphine in normal mice is blocked by ultra-low dose naltrexone, unmasking potent opioid analgesia," *Brain Research* 888:75-82, Elsevier Science B.V., Netherlands (2001).

Data Sheet "SUBOXONE" (buprenorphine + naloxone), Mar. 2006, 11 pages.

Eissenberg, T., et al., "Buprenorphine's Physical Dependence Potential: Antagonist-Precipitated Withdrawal in Humans," *J Pharmacol Exp Ther* 276(2):449-459, Williams & Wilkins, United States (1996).

Elkader, A. and Sproule, B., "Buprenorphine Clinical Pharmacokinetics in the Treatment of Opioid Dependence," *Clin Pharmacokinet* 44(7):661-680, Adis Data Information B.V., New Zealand (2005).

Fink, M., et al., "Naloxone in heroin dependence," *Clin Pharmacol Ther* 9(5):568-577, Wiley, United States (1968).

Fishman, J., et al., "Disposition of Naloxone-7-8-H in Normal and Narcotic-Dependent Men," *The Journal of Pharmacology and Experimental Therapeutics* 187(3):575-580, The Williams & Wilkins Co., United States (1973).

Fudala, P.J., et al., "Effects of buprenorphine and naloxone in morphine-stabilized opioid addicts," *Drug and Alcohol Dependence* 50:1-8, Elsevier Science Ireland Ltd., Ireland (1998).

Gerra, G., et al., "Clonidine and Opiate Receptor Antagonists in the Treatment of Heroin Addiction," *Journal of Substance Abuse Treatment* 12(1):35-41, Elsevier Science Ltd., England (1995).

Gonzalez, J.P. and Brodaen, R.N., "Naltrexone a Review of its Pharmacodynamic and Pharmacokinetic Properties and Therapeutic Efficacy in the Management of Opioid Dependence," *Drug* 35:192-213, ADIS Press Limited, New Zealand (1988).

Greenwald, M.K., et al., "Comparative Clinical Pharmacology of Short-Acting *Mu* Opioids in Drug Abusers ," *The Journal of Pharmacology and Experimental Therapeutics* 277:1228-1236, The American Society for Pharmacology and Experimental Therapeutics, United States (1996).

Harris, D.S., et al., "Buprenorphine and naloxone co-administration in opiate-dependent patients stabilized on sublingual buprenorphine," *Drug and Alcohol Dependence* 61:85-94, Elsevier Science Ireland Ltd., Ireland (2000).

Hussain, M.A., et al., "Buccal and oral bioavailability of naloxone and naltrexone in rats," *International Journal of Pharaceutics* 36:127-130, Elsevier B.V., Netherlands (1987).

Johnson R.E., et al., "Buprenorphine and Naloxone for Heroin Dependence," *Current Psychiatry Reports* 2:519-526, Current Sciences Inc., United States (2000).

Kosten, T.R., et al., "Opioid antagonist challenges in buprenorphine maintained patients," *Drug and Alcohol Dependence* 25:73-78, Elsevier Scientific Publishers Ireland Inc., Ireland (1990).

Kuhlman, J.J., et al., "Human Pharmacokinetics of Intravenous, Sublingual, and Buccal Buprenorphine," *Journal of Analytical Toxicology* 20:369-378, Oxford University Press, United States (1996).

Lehmann, K.A., et al., "Influence of Naloxone on the Postoperative Analgesic and Respiratory Effects of Buprenorphine," *Eur J Clin Pharmacol* 34:343-352, Springer-Verlag, Germany (1988).

Mendelson, J., et al., "Bioavailability of Sublingual Buprenorphine," *J Clin Pharmacol* 37:31-37, Hall Associates, England (1997).

Mendelson, J., et al., "Buprenorphine and naloxone combinations: the effects of three dose ratios in morphine-stabilized, opiate-dependent volunteers," *Psychopharmacology* 141:37-46, Springer-Verlag, Germany (1999).

Mendleson, J., et al. "Buprenorphine and naloxone interactions in opiate-dependent volunteers," *Clin Pharmacol Ther* 60:105-114, Wiley, United States (1996).

Mendleson, J., et al., "Buprenorphine and Naloxone Interactions in Methadone Maintenance Patients," *Biol Psychiatry* 41:1095-1101, Society of Biological Psychiatry, Elsevier, United States (1997).

Parwatikar, S.D., et al., "Methadone-naloxone in combination for the treatment of heroin addicts," *Clin Pharmacol Ther* 14(6):941-948, Wiley, United States (1973).

Preston, K.L., et al., "Buprenorphine and naloxone alone and in combination in opioid-dependent humans," *Psychopharmacology* 94:484-490, Springer-Verlag, Germany (1988).

Preston, K.L., et al., "Effects of sublingually given naloxone in opioid-dependent human volunteers," *Drug and Alcohol Dependence* 25:27-34, Elsevier Scientific Publishers Ireland Ltd., Ireland (1990).

Robinson, S.E., "Buprenorphine: An Analgesic with an Expanding Role in the Treatment of Opioid Addiction," *CNS Drug Reviews* 8(4):377-390, Neva Press, United States (2002).

Schuh, K.J., et al., "Onset, magnitude and duration of opioid blockade produced by buprenorphine and naltrexone in humans," *Psychopharmacology* 145:162-174, Springer-Verlag, Germany (1999).

Shojaei, A.H., "Buccal Mucosa as a Route for Systemic Drug Delivery: A Review," *J Pharm Pharm Sci* 1(1):15-30, The Society, Canada (1998).

Stoller, K.B., et al., "Effects of buprenorphine/ naloxone in opioid-dependent humans," *Psychopharmacology* 154:230-242, Springer-Verlag, Germany (2001).

Strain, E.C., et al., "Effects of burprenorphine versus buprenorphine/ naloxone tablets in non-dependent opioid abusers," *Psychopharmacology* 148:374-383, Springer-Verlag, Germany (2000).

Suboxone (CIII) buprenorphine HC1 and naloxone HC1 dihydrate sublingual tablets insert, Sep. 2006, 4 pages.

Weinhold, L.L., et al., "Buprenorphine alone and in combination with naloxone in non-dependent humans," *Drugs and Alcohol Dependence* 30:263-274, Elsevier Scientific Publishers Ireland Ltd., Ireland (1992).

"Suboxone : EPAR—Scientific Discussion," published by EMEA on Oct. 19, 2006, 42 pages.

Das, N.G. and Das, S.K., "Development of Mucoadhesive Dosage Forms of Buprenorphine for Sublingual Drug Delivery," *Drug Delivery* 11:89-95, Informa Healthcare, England (2004).

Matharu, R.P., et al., "Development and Stability Assessment of Buprenorphine Sublingual Tablets for the Treatment of Opiate Addiction," *Pharmaceutical Research* 9(10):S128, Plenum Press, United States (1992) (Abstract No. PT 6056).

"Pharmaceutical Technical Procedures," in *European Pharmacopoeia Fourth Edition Supplement 4.1*, pp. 106-107 and 194-197, Counsel of Europe, France (2001).

"Pharmaceutical Technical Procedures," in *European Pharmacopoeia Third Edition*, pp. 127-131, Counsel of Europe, France (1997).

Drugs@FDA: FDA Approved Drug Products, "Suboxone" FDA Application No. (NDA) 020733, 26 pages.

RB Pharmaceuticals Limited, "Temgesic 200 microgram Sublingual tablets," 6 pages, Rechick Benckiser Healthcare (Oct. 2013).

(56) References Cited

OTHER PUBLICATIONS

RB Pharmaceuticals Limited, "Temgesic 400 microgram Sublingual tablets," 7 pages, Rechick Benckiser Healthcare (Oct. 2013).
Jenkinson, R.A., et al., "Buprenorphine diversion and injection in Melbourne, Australia: an emerging issue?" *Addiction* 100:197-205, Society for the Study of Addiction, Australia (2004).
Patent and Exclusivity Search Results "Orange Book: Approved Drug Products with Therapeutic Equivalence Evaluations," 3 pages, accessed on Jan. 8, 2013.
"Ondansetron-RL™ Zydis® Wafers," Consumer Medicine Information Leaflet, 5 pages, accessed on Feb. 19, 2013.
"Test of disintegration time for buprenorphine tablets," Document ID PID 2013-302, 8 pages, dated Dec. 12, 2013.
"Suboxone (CIII) (buprenorphine HC1 and naloxone HC1 dihydrate sublingual tablets) and Subtex (CIII) (buprenorphine HC1 sublingual tablets)" Prescribing Information, 48 pages.
Bredenberg, S., et al., "In vitro and in vivo evaluation of a new sublingual tablet system for rapid oromucosal absorption using fentanyl citrate as the active substance," *European Journal of Pharmaceutical Sciences* 20:327-334, Elsevier B.V., Netherlands (2003).
Guo, J-H, "Bioadhesive Polymer Buccal Patches for Buprenorphine Controlled Delivery Formulation, In-vitro Adhesion and Release Properties," *Drug Development and Industrial Pharmacy* 20(18):2809-2821, Marcel Dekker, Inc., United States (1994).
"Pharmacology of Buprenorphine," in *The Treatment of Opioid Dependence*, Strain, E.C. and Stitzer, M.L., eds., pp. 216-219, Johns Hopkins University Press, United States (2006).
Chawarski, M.C., et al., "Plasma concentrations of buprenorphine 24 to 72 hours after dosing," *Drug and Alcohol Dependence* 55:157-163, Elsevier Science Ireland Ltd., Ireland (1999).
Schuh, K.J. and Johanson, C-E., "Pharmacokinetic comparison of the buprenorphine sublingual liquid and tablet," *Drug and Alcohol Dependence* 56:55-60, Elsevier Science Ireland Ltd., Ireland (1999).
Suboxone Prescribing Information, revised Dec. 2011, 21 pages.
Unknown Author "Reckitt Benckiser Pharma Voluntarily Withdraws Suboxone for Heroin Treatment," 1 page, accessed on Dec. 26, 2013.
"Background Information on the Procedure," Suboxone buprenorphine/ naloxone, 2 pages accessed on Dec. 20, 2013.
Notice of Opposition to European Patent 2059243 B1, Opponent Hexal AG, 23 pages, Dec. 17, 2013.
Notice of Opposition to European Patent 2059243 B1, Opponent Orexo AB, 235 pages, Dec. 19, 2013.
Notice of Opposition to European Patent 2059243 B1, Opponent Alison Gallafent, 150 pages, Dec. 21, 2013.
Notice of Opposition to European Patent 2059243 B1, Opponent Ethypharm, 85 pages, Dec. 26, 2013.
English translation of the Notice of Opposition to European Patent 2059243 B1, Opponent Ethypharm, 24 pages, Dec. 26, 2013.
Proprietor's Response to Notices of Opposition During Opposition Procedure in European Patent 2059243 B1, 45 pages, Aug. 22, 2014.
US 5,120,549, 06/1992, Gole et al. (withdrawn)

* cited by examiner

BUPRENORPHINE-WAFER FOR DRUG SUBSTITUTION THERAPY

The present invention relates to oral pharmaceutical dosage forms comprising buprenorphine with the dosage form releasing buprenorphine instantly upon oral, preferably sublingual, application of the dosage form. The present invention also relates to the use of such dosage forms for treating pain in a human or animal or for drug substitution therapy in drug-dependent human subjects.

BACKGROUND OF THE INVENTION

Chronic pain, which may be due to idiopathic reasons, cancer or other diseases such as rheumatism and arthritis, is typically treated with strong opioids.

Over the last decades prejudices in the medical community as to the use of strong opioids for treating chronic pain in patients has significantly decreased. Many of these prejudices were due to some of the characteristics being inherent to opioids.

While opioids have always been known to be useful in pain treatment, they also display an addictive potential in view of their euphorigenic activity. Thus, if opioids are taken by healthy human subjects with a drug seeking behaviour they may lead to psychological as well as physical dependence.

These usually undesired characteristics of opioids can however become important in certain scenarios such as drug substitution therapies for drug addicts. One of the fundamental problems of illicit drug abuse by drug addicts ("junkies") who are dependent on the constant intake of illegal drugs such as heroin is the drug-related criminal activities resorted to by such addicts in order to raise enough money to fund their addiction. The constant pressures upon addicts to procure money for buying drugs and the concomitant criminal activities have been increasingly recognised as a major factor that counteracts efficient and long-lasting withdrawal and abstinence from drugs.

Therefore, programmes have been developed, particularly in the United States and western European countries, in which drug addicts are allowed to take prescription drugs under close supervision of medical practitioners instead of illegal drugs such as street heroin.

The aim of drug substitution theory is thus to first enable addicts to lead a regular life by administering legal drugs to prevent withdrawal symptoms, but because of their legal character and prescription by medical practitioners do not lead to the aforementioned described drug-related criminal activities. In a second and/or alternate step in the treatment of drug addiction may be to slowly make the drug addict less dependent on the drug by gradually reducing the dose of the substitution drug or to bridge the time until a therapy place in a withdrawal programme is available.

The standard drug used in drug substitution therapy programmes has for a long time been methadone. However, in recent years the potential of other opioids as substitution drugs in substitution therapy has been recognised. A particularly suitable drug for that purpose is the opioid buprenorphine, which is a mixed opioid agonist/antagonist.

Nowadays, buprenorphine preparations are administered in drug substitution programmes in the form of a tablet for sublingual administration. One of the reasons that the tablets are formulated for sublingual administration is that this the preferred route of administration for buprenorphine. Furthermore, if a patient swallows such tablets they will not provide euphorigenic activity.

One example of sublingual tablets for drug substitution therapy is the preparation Subutex® (being marketed in Germany by Essex Pharma).

Nevertheless, drug addicts sometimes still try to divert these sublingual buprenorphine tablets by removing them from the mouth when the supervising healthcare professional's attention is directed to other activities. Later the tablets may be sold or the active agent buprenorphine isolated/extracted to apply it parenterally.

Another buprenorphine preparation aimed at preventing this potential possibility of abuse has recently gained administrative approval in the United States (Suboxone®). The Suboxone® preparation comprises buprenorphine hydrochloride and the opioid antagonist naloxone hydrochloride dihydrate. The presence of naloxone is intended to prevent parenteral abuse of buprenorphine as parenteral co-administration of buprenorphine and naloxone in e.g. an opioid-dependent addict will lead to serious withdrawal symptoms.

However, there remains a need for other diversion and/or abuse-resistant dosage forms of buprenorphine, which can be used in drug substitution therapy as described above. Additionally, it would be desirable to have a buprenorphine preparation available which is diversion and/or abuse-resistant in cases where the preparation is used for drug substitution therapy and which could also provide efficient analgesia in cases where the preparation is administered to alleviate pain in a patient.

OBJECT AND SUMMARY OF THE INVENTION

It is an object of the present invention to provide an oral pharmaceutical dosage form of the active agent buprenorphine that is less prone to diversion and/or abuse in drug substitution therapy. It is another object of the present invention to provide an oral dosage form of the active agent buprenorphine that can be used for drug substitution therapy and/or pain treatment.

In one embodiment the present invention relates to an oral pharmaceutical dosage form comprising at least buprenorphine or a pharmaceutically acceptable salt thereof with a dosage form releasing buprenorphine or said pharmaceutically acceptable salt thereof instantly upon or oral, preferably sublingual, application of the dosage form. It is, however, understood that the invention and its various embodiments which are set out below, can be extended to any opioid or analgesic whose preferred route of administration is oral, preferably sublingual, as is the case for buprenorphine.

An instant release of buprenorphine or a pharmaceutically acceptable salt thereof upon oral, preferably sublingual, application means that substantially all of the buprenorphine or said pharmaceutically acceptable salt thereof will be released within less than three minutes, preferably within less than two minutes or less than one minute. Even more preferably, substantially all of the buprenorphine or said pharmaceutically acceptable salt thereof will be released within less than thirty seconds, twenty seconds, ten seconds or even within less than five seconds after oral, preferably sublingual, application of the dosage form. In one of the preferred embodiments these oral dosage forms will comprise between approximately 0.1 mg and approximately 16 mg buprenorphine or the equivalent amounts of a pharmaceutically acceptable salt thereof.

In a further preferred embodiment these oral pharmaceutical dosage forms will achieve an average $C_{max}$ of between 1.5 ng/ml and approximately 2.25 ng/ml in the case of a dose of 0.4 mg buprenorphine hydrochloride being administered. In the case of a dose of 8 mg buprenorphine HCl being administered, the $C_{max}$ will typically be between approximately 2.5 and 3.5 ng/ml and if a dose of 16 mg buprenorphine hydrochloride is administered the $C_{max}$ will preferably be between 5.5 to 6.5 ng/ml.

Yet another preferred embodiment of the invention relates to oral pharmaceutical dosage forms which may provide for the above-mentioned characteristics and/or an average $T_{max}$ of from approximately 45 to approximately 90 minutes.

In a particularly preferred embodiment the dosage forms will additionally comprise an opioid antagonist, preferably naloxone or a pharmaceutically acceptable salt thereof.

In yet a further preferred embodiment, the pharmaceutical dosage form will comprise buprenorphine and the opioid antagonist, which preferably is naloxone, in a weight ratio of from approximately 1:1 to approximately 10:1.

One embodiment of the present invention also relates to oral pharmaceutical dosage forms, which may have some or all of the aforementioned characteristics and wherein the dosage form has a film-like or wafer-like shape.

Another embodiment relates to a method of manufacturing the afore-mentioned described dosage forms.

Embodiments of the present invention also relate to the use of the afore-described oral, preferably sublingual, pharmaceutical dosage forms in the manufacture of a medicament for treating pain in a human or animal and/or for drug substitution therapy in drug-dependent human subjects.

One aspect of the invention also relates to a method of drug substitution therapy in drug-dependent human subjects wherein the aforementioned oral pharmaceutical dosage forms are administered to a drug-dependent subject in need thereof.

DETAILED DESCRIPTION OF THE INVENTION

From the prior art, sublingual tablets are known under the trade names Subutex® or Suboxone® both of which comprise the active agent buprenorphine hydrochloride for drug substitution therapy.

The suitability of particularly buprenorphine for drug substitution therapy had been recognised early on in view of buprenorphine's very long elimination half-life (reported as approximately 20 to 37 hours), which allows a reduced frequency of administration. As a consequence drug addicts who participate in drug substitution therapy have to report less frequently to the medical agency or healthcare professional supervising the substitution programme.

Furthermore, the sublingual absorption of buprenorphine has the advantage that an abuse by swallowing tablets of buprenorphine is less likely to occur. The tablets that are currently on the market in the form of Subutex® and Suboxone® preparations are both for sublingual administration and typically disintegrate over a time period of five to ten minutes. However, within that time period the drug addict may be able to divert the tablet before subsequently either selling the tablets on the street or isolating the active agents therefrom.

In order to reduce of eliminate these problems, the present invention provides oral pharmaceutical dosage forms which comprise the active agent buprenorphine and which release buprenorphine instantly after oral, preferably sublingual, administration of the drug.

It is understood that if reference is made in the context of this invention to the term "buprenorphine" this refers to the free base as well as to any pharmaceutically acceptable salt thereof such as the hydrochloride, sulfate, bisulfate, tartrate, nitrate, citrate, bitartrate, phosphate, malate, maleate, hydrobromide, hydroiodide, fumarate, succinate salts and the like.

A particularly preferred pharmaceutically acceptable salt of buprenorphine is buprenorphine hydrochloride.

The provision of a pharmaceutical dosage form comprising buprenorphine or a pharmaceutically acceptable salt thereof in e.g. film-like or wafer-like shapes which allows for instant release of the active agent upon oral, preferably sublingual, administration of the dosage form should prevent the type of abuse resulting from illicit diversion of the tablets by drug addicts participating in drug substitution therapy programmes.

In the context of the present invention instant release means that substantially the whole amount of the buprenorphine or the respective pharmaceutically acceptable salt thereof will be released in less than five minutes. Preferably, substantially all of the buprenorphine or its pharmaceutically acceptable salt thereof will be released within less than four, within less than three, within less than two and more preferably within less than one minute.

In a particularly preferred embodiment, instant release refers to the situation that substantially all of the buprenorphine or the respective pharmaceutically acceptable salt thereof will be released within less than thirty seconds, within less than twenty seconds, or within less than ten seconds. In an even more preferred embodiment, the term "instant release" means that substantially all of the buprenorphine will be released from the dosage form within less than five seconds or within less than three seconds.

The term "substantially all" means that approximately 95% of the drug will have been released.

The term "approximately" in the context of the present invention describes a deviation from the indicated value of 10% and preferably of 5%.

Such efficient release of the drug is hard to achieve with a sublingual tablet which generally requires a greater amount of time to melt or to disintegrate.

Fast-dissolving or rapidly disintegrating dosage forms for other pharmaceutically active compounds are known which disintegrate within seconds upon contact with the mucosal saliva of the mouth and particularly the sublingual mucosa.

These pharmaceutical dosage forms and formulation principles are well known to the person skilled in the art and will be described in more detail below.

As regards the dosage amount, the pharmaceutical compositions in accordance with the present invention will typically comprise between approximately 0.1 mg and approximately 16 mg of buprenorphine or a pharmaceutically acceptable salt thereof such as buprenorphine hydrochloride. Preferred dosage amounts will be in the range of between approximately 0.4 mg and approximately 12 mg or between approximately 2 mg and approximately 8 mg buprenorphine or a pharmaceutically acceptable salt thereof.

The oral pharmaceutical dosage forms in accordance with the invention may have the further characteristic of providing a $C_{max}$ of approximately 1.5 to 2.5 ng/ml in the case of a dose of 4 mg buprenorphine hydrochloride being administered. A preferred $C_{max}$ in the case of a dose of 4 mg of buprenorphine hydrochloride being administered may be approximately between 1.7 ng/ml to 2 ng/ml.

In the case of a dose of 8 mg buprenorphine hydrochloride being administered, the $C_{max}$ may be approximately between 2.5 and 3.5 ng/ml. In a preferred embodiment the $C_{max}$ may be approximately between 2.75 ng/ml and 3.25 ng/ml in the case of a dose of 8 mg buprenorphine hydrochloride being administered.

In case of a dose of 16 mg buprenorphine hydrochloride being administered, the $C_{max}$ may preferably be in the range of approximately 5 to 7 ng/ml. In a preferred embodiment the $C_{max}$ may be between 5.5 and 6.5 ng/ml if 16 mg of buprenorphine hydrochloride are administered.

The $AUC_{0-48}$ (i.e. the Area under the Curve for 48 hours after administration) may in the case of administration of 4 mg of buprenorphine hydrochloride be in the range of approximately 10 to 15 hours×ng/ml. In a preferred embodiment the $AUC_{0-48}$ may be approximately 12 to 13 hours×ng/ml. In the case of 8 mg buprenorphine hydrochloride being administered the $AUC_{0-48}$ may be approximately in the range of 15 to 25 hours×ng/ml. In a preferred embodiment the $AUC_{0-48}$ in this case may be between approximately 20 to 22 hours×ng/ml. In the case of 16 mg buprenorphine hydrochloride being administered, the $AUC_{0-48}$ may be in the range of 25 to 40 hours×ng/ml. In a preferred embodiment the $AUC_{0-48}$ in this case may be in the range of approximately 30 to 35 hours×ng/ml.

The average $T_{max}$ values for such preparations will preferably be from approximately 45 to approximately 90 minutes.

It is understood that the aforementioned pharmacokinetic parameters $C_{max}$ and $AUC_{0-48}$ are average values that are obtained by measuring the blood plasma levels in a group of eight to approximately twenty-four patients. These patients will be selected according to inclusion and exclusion criteria, as they are common for drug substitution programmes. It is understood that such patients typically will be of average weight and Caucasian origin.

The pharmaceutical dosage form in accordance with the invention will be administered such that the maximal dosage per day is 32 mg of buprenorphine. Once a patient is enrolled in substitution therapy, the initial dosage will be typically between 2 mg to 4 mg of buprenorphine. The formulations may be administered once a day, every two days, preferably every three days or even less frequently.

In a preferred embodiment, the oral dosage forms of the invention will additionally comprise an opioid antagonist. Such antagonists may be selected from the group comprising naltrexone, naloxone, nalmefene, nalorphine, nalbuphine, naloxoneazinen, methylnaltrexone, ketylcyclazocine, norbinaltorphimine, naltrindol, 6-β-naloxol and 6-β-naltrexol or the pharmaceutically acceptable salts thereof.

Especially preferred antagonists comprise naltrexone, nalmefene and naloxone. Specifically preferred as an antagonist is naloxone and its hydrochloride salt.

It is understood, that if in the context of the present invention reference is made to an opioid antagonist, this also not only refers to the free base but also to pharmaceutically acceptable salts thereof such as those mentioned for buprenorphine.

A particularly preferred antagonist is naloxone. Of the naloxone salts, naloxone hydrochloride dihydrate may be particularly preferable in combination with buprenorphine hydrochloride.

The pharmaceutical dosage forms in accordance with the invention will comprise buprenorphine and the antagonist, which preferably is naloxone, in a weight ratio of from 1:1 to 10:1. A weight ratio of from 2:1 to 8:1 may be preferred, with a weight ratio of 4:1 being particularly preferred.

Thus, if an oral dosage form in accordance with the present invention for example comprises 2 mg buprenorphine hydrochloride it will comprise approximately 0.5 mg naloxone. If the dosage form comprises 0.4 mg buprenorphine hydrochloride, it will comprise 0.1 mg naloxone and if the dosage form comprises 8 mg buprenorphine hydrochloride it will comprise e.g. 2 mg naloxone hydrochloride.

A particularly preferred embodiment thus relates to an oral dosage form comprising buprenorphine, preferably buprenorphine hydrochloride, and naloxone, preferably naloxone hydrochloride, wherein the dosage form releases said active agents within less than one minute, preferably within less than thirty seconds and more preferably within less than ten seconds after sublingual application of the dosage form. In addition, the dosage forms may provide the preferred values of the aforementioned pharmacokinetic parameters $C_{max}$, and $AUC_{0-48}$.

Thus, the person skilled in the art will have to ensure that indeed an oral dosage form is used which is able to allow for incorporation of sufficient amounts of buprenorphine and preferably also of naloxone and which at the same time disintegrates rapidly enough to release the active agents instantly.

In one embodiment one may use non-gelatin film materials, e.g. films of modified cellulose materials as dosage forms. In this case, buprenorphine and optionally opioid antagonists such as naloxone are incorporated into the film matrix and films thus prepared may be administered orally.

In accordance with this aspect of the invention, the active ingredients may be dissolved in a hydrophilic, organic system to form a homogenous solution or dispersion. The solution or dispersion can then be applied to one or more surfaces of a non-gelatin polymeric film, e.g. a dry cellulose ether film, resulting in the active ingredient(s) and/or liquid carrier phase being transported through the surface of the "dry" film resulting in a new film composition.

The film substrate may remain completely intact or relatively physically unchanged immediately following the incorporation process. It can, however, be converted to any size or shape of unit dosage form. Alternatively, the film substrate may liquefy or dissolve partly or fully during the incorporation process, but nevertheless finally forming a single discrete film, after curing. Films according to this aspect of the invention are typically made up of one or more soluble polymer or polymers which will otherwise degrade at the intended site of release after administration in the mouth, e.g. sublingual administration, in order to provide the instant release of the active agents. Suitable cellulose ether film bases include e.g. hydroxypropylmethylcellulose (HPMC), hydroxypropylcellulose (HPC), hydroxyethylmethylcellulose (HEMC), hydroxyethylcellulose (HEC), methylcellulose (MC), carboxymethylcellulose (CMC) and salts and derivates of all of the aforesaid materials. A particularly suitable cellulose ether for forming the film is HPMC.

Optional ingredients may be added including colorants, emulsifiers, humectants, and anti-blocking agents.

Once one has a film being based on a cellulose ether available, in a next step the active ingredient(s) will be applied in the form of a liquid to the film. Appropriate means of liquid application onto the film substrate include extrusion, roller application, pouring, spraying, brush painting or whipping. Further details of the preparation of such films can be taken e.g. from WO 2005/079750 A2 which is incorporated by reference herewith.

Another possible technology in order to provide the aforedescribed pharmaceutical dosage forms of buprenorphine and preferably naloxone is described in WO 03/030883. In this latter embodiment of the present invention, a thin film drug delivery composition includes (i) a flowable water-soluble film-forming matrix and (ii) the active agent(s) uniformly stationed therein. Optionally a taste-masking agent may be coated or intimately associate with the active agent(s) to provide taste masking of the active agent(s). The flowable water-soluble film-forming matrix together with the active agent(s) is formable into a dry film of less than about 380 microns in thickness, for example less than about 250 microns in thickness.

The matrix may be a cellulosic material, a gum, a protein, a starch, a glucan and combinations thereof. For example one may use the already aforementioned methylcellulose, HMC, HEC, HC, HPC, HPMC, HMPC, gum Arabic, xanthan gum etc. The films are prepared according to standard technology and the active agents are displaced thereon and therein as described in WO 03/030883.

Yet another interesting technology relates to immediate release drug delivery forms as described in WO 99/17744, which is also incorporated by reference herein as far as it describes fast releasing oral dosage forms. The person skilled in the art will understand that the processes and dosage forms in WO 99/17744 may be used to obtain the aforementioned described pharmaceutical dosage forms of buprenorphine and preferably also naloxone.

One may of course also use fast disintegrating tablets that disintegrate upon contacting the saliva, e.g. under the tongue, following oral administration. Such fast-disintegrating tablets are described e.g. in WO 99/44580 and are well known to the person skilled in the art.

A particularly interesting technology for fast-releasing dosage forms that may be used for the purpose of the present invention to provide an oral dosage form of buprenorphine and preferably an opioid antagonist such as naloxone can be taken from WO 96/26720.

Therein it is described how the active agent selegiline is formulated into a rapidly releasing dosage form that can be used e.g. for sublingual administration. WO 96/26720 describes in detail a "fast-dispersing dosage form" with the term encompassing all types of dosage forms being described in U.S. Pat. No. 5,120,549, U.S. Pat. No. 5,079,018, WO 93/12769, U.S. Pat. No. 5,298,261 and WO 91/04757.

As for WO 96/26720 in the case of the active agent selegiline, the present invention contemplates particularly using fast-dispersing dosage forms as described in UK patent number 1548022, that is, a solid fast-dispersing dosage form comprising a network of the active ingredient(s) and a water-soluble or water-dispersible carrier which is inert towards the active ingredient, the network having been obtained by subliming solvent from a composition in the solid state, that composition comprising the active ingredient and a solution of the carrier in a solvent.

It is preferred that such a composition in accordance with the invention disintegrates within one to ten seconds, and particularly within two to eight seconds of being placed in the oral cavity and particularly sublingually.

The composition will preferably contain in addition to the active ingredient, matrix forming agents and secondary components.

Matrix forming agents suitable for use in this aspect of the present invention include materials derived from animal or vegetable proteins, such as gelatins, dextrins and soy, wheat and psyllium seed proteins, gums such as acacia, guar, agar, and xanthan, polysaccharides, alginates, carboxymethylcelluloses, carrageenans, dextrans, pectins, synthetic polymers such as polyvinylpyrrolidone, and polypeptide/protein or polysaccharide complexes such as gelatin-acacia complexes.

Other matrix forming agents suitable for use in the present invention include sugars such as mannitol, dextrose, lactose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

One or more matrix forming agents may be incorporated into the solution or suspension prior to solidification. The matrix forming agent may be present in addition to a surfactant or to the exclusion of a surfactant. In addition to forming the matrix, the matrix forming agent may aid in maintaining the dispersion of any active ingredient within the solution or suspension.

Secondary components such as preservatives, antioxidants, surfactants, viscosity enhancers, colouring agents, flavouring agents, pH modifiers, sweeteners or taste-masking agents may also be incorporated into the composition. Suitable colouring agents include red, black and yellow iron oxides. Suitable flavouring agents include mint, raspberry, liquorice, orange, lemon, grapefruit, caramel, vanilla, cherry and grape flavours and combinations of these. Suitable pH modifiers include citric acid, tartaric acid, phosphoric acid, hydrochloric acid and maleic acid. Suitable sweeteners include aspartame and thaumatin. Suitable taste-masking agents include sodium bicarbonate, ion-exchange resins, cyclodextrin inclusion compounds, adsorbates or microencapsulated actives.

Such fast-dispersing dosage forms containing buprenorphine and preferably an opioid antagonist such as naloxone may be similarly obtained as described in GB 1548022B or WO 96/26720, in particular Example 1 of the latter, which are incorporated herein in their entirety.

A particularly preferred embodiment of the present invention relates to dosage forms, which are produced along the lines described in WO 03/070227 A1.

This prior art reference describes taste-masked, film-type or wafer-type medicinal preparations. It is to be understood that the dosage forms in accordance with the present invention may preferably be such film-type or wafer-type medicinal preparations with the taste-masking being only an optional feature.

Flat active agent carriers that have a film-type or wafer-type structure provide for various advantages. As a consequence of the low thickness in comparison to the surface area, there is only a short diffusion pathway if such a dosage form is applied e.g. to the mucosa of the oral cavity. This typically leads to a very rapid release of the active agents which can then be quickly, efficiently and directly absorbed by the mucosa of the oral cavity and particularly sublingually if the active agent is absorbable at all via that route. Thus, in case of buprenorphine such very flat film-type or wafer-type dosage forms are highly desirable as they will allow for the provision of an instant release of active ingredient, thereby minimising the abuse problems encountered with the formulations of the prior art.

Flat active agent carriers have been developed for different purposes. One of the basic prior art references in this context is DE 27 46 414 in which active agent, binding agent and additional excipients are processed to yield a dosage form in the form of film-type strand.

One of the advantages of wafer-type pharmaceutical dosage forms as described in WO 03/070227 A1 is that there is a direct correlation between the amount of the active agent and the length of a certain part of the strand in view of the homogenous thickness, density and width. Thus, one can easily obtain a certain unit dosage by simply cutting the wafer-like dosage form in to appropriately sized pieces.

Such film-type or wafer-type dosage forms in accordance with the present invention are characterised in that they comprise a matrix which is formed from at least one matrix-forming polymer and in which buprenorphine and preferably an opioid antagonist such as naloxone are dissolved or homogenously dispersed.

The rapidly disintegrating matrix of the pharmaceutical dosage forms in accordance with the invention comprises as one of its basic substances water-soluble polymers or mixtures of such polymers. Preferably synthetic or partially synthetic polymers or naturally occurring biopolymers are used which can form films and are water-soluble. Particularly suitable for this purpose are polymers which may be selected from the group comprising cellulose derivatives, polyvinylalcohol, polyacrylates and polyvinylpyrrolidone.

Within the cellulose derivatives, hydroxypropylmethylcellulose, carboxymethylcellulose, sodium carboxymethylcellulose, hydroxyethylcellulose, hydroxypropylcellulose, methylcellulose, and hydroxypropylmethylcellulose may be used. One may also use water-soluble polysaccharides being derived from plants or microbes. Preferred polysaccharides include pullulan, trantan, alginate, dextrin and pectins.

One may also use proteins and preferably gelatin or other gel-forming proteins. One may also use starch and starch derivatives, gelatin, polyvinylpyrrolidone, gum Arabic, pullulan, acrylates, polyethylene oxide with a particular focus on polyox 10, polyox 80, polyox 205, polyox 301, polyox 750 or copolymers of methylvinylether and maleic acid anhydride.

The person skilled in the art will appreciate that the extent to which buprenorphine and optionally an opioid antagonist such as naloxone are instantly released depends in part on the type of matrix-forming polymer chosen. For example, a dosage form using polyvinylalcohol as matrix-forming polymer may disintegrate faster than a dosage form using HPMC as matrix-forming polymer. The disintegration time may be adjusted by mixing a combination of different polymers in suitable amounts.

The person skilled in the art also knows disintegrating agents, which can "pull" water into the matrix which then pushes the dosage forms apart. Thus, such disintegrating agents may also be used for adjustment of the disintegration time.

In order to allow absorption of buprenorphine over the mucosa of the mouth, and particularly sublingually, in one embodiment the dosage forms may additionally use agents that enhance absorption of the active agent, i.e. so-called permeation enhancers.

Such permeation enhancers may be selected from the group comprising propandiol, dexpanthenol, and oleic acid. The permeation enhancers may also be selected from the group comprising saturated or unsaturated fatty acids, hydrocarbons, linear or branched fatty alcohols, dimethylsulfoxide, propylene glycol, decanol, dodecanol, 2-octyldodecanol, glycerine, ethanol or other alcohols.

According to a preferred embodiment the film-type or wafer-type oral dosage forms of the present invention in the presence of saliva can disintegrate within e.g. one second to three minutes or within five seconds to one minute or five seconds to thirty seconds.

The disintegration times of the oral dosage forms in accordance with the invention are measured according to the European pharmacopoeia, 4$^{th}$ edition 2002.

In the present case where the active agent buprenorphine is administered sublingually, the dosage forms in accordance with the invention may additionally comprise an excipient that mediates adhesion to the respective mucosa. Examples of such muco-adhesive substances are e.g. polyacrylic acid, carboxymethylcellulose, hydroxymethylcellulose, methylcellulose, alginic acid, gelatin and gum Arabic.

The thickness of the film-type or wafer-type dosage forms in accordance with the invention may typically be between 5 µm and 10 mm, 30 µm and 2 mm, or 0.1 mm and 1 mm. The dosage forms may be round, oval, elliptic, or may have a triangular, quadrangular, or multi-angular form. Typically the surface of the pharmaceutical dosage forms in accordance with the invention is flat.

As stated above, the film-type or wafer-type matrix of the dosage forms of this aspect of the invention comprises at least one matrix-forming polymer. The matrix-forming polymer(s) are an essential component of the matrix.

The polymer amount within the matrix may be between approximately 3% by weight and approximately 98% by weight and preferably between 7 and 80% by weight and even more preferably between 20 and 50% by weight, the weight percentages being based on the total weight of the dosage forms.

The mucoadhesive properties as well as the disintegrating properties are to a large extent determined by the type of matrix-forming polymer(s), as well as the relative amount of the polymer(s) used in the dosage forms.

Besides the matrix-forming polymers, buprenorphine and optionally an opioid antagonist, further excipients may be present within the matrix.

These additional excipients may be filling agents such as $SiO_2$, colorants and pigments (such as $TiO_2$) disintegrating agents particularly those which attract water (such Aerosil), emulsifying agents, plasticizers, sweeteners or conserving agents. Additionally, auxiliary excipients such as stabilising agents or antioxidants may be added.

If a taste-masking effect is to be obtained, the dosage form in accordance with this aspect of the invention may comprise additionally a carbon dioxide-forming agent that upon contact with the saliva develops carbon dioxide. Such carbonates are well known in the prior art from effervescent formulations and include e.g. sodium hydrogen carbonate, sodium carbonate, potassium hydrogen carbonate or potassium carbonate. In order to enhance $CO_2$ development, one may add acidic components such as e.g. sodium dihydrogen- or disodiumhydrogen phosphate, sodium tartrate, sodium ascorbate etc. One may of course also use citric acid, tartaric acid, adipinic acid, ascorbic acid, acetic acid, lactic acid etc.

Thus, one preferred embodiment of the invention relates to oral dosage forms of film-type or wafer-type film as described above which comprise buprenorphine and optionally an opioid antagonist such as naloxone with the oral dosage form having the above-described characteristics as to the amount of buprenorphine and the optional antagonist, the pharmacokinetic parameters $C_{max}$ and $AUC_{0-48}$ and the instant release of the active agents from the dosage form. The person skilled in the art will know how to produce such film-type or wafer-type dosage forms on the basis of the above-mentioned information. This may be achieved by common film-coating technologies, extrusion processes, spray drying etc. More details can be taken from WO 03/070227.

The person skilled in the art will also know other dosage forms, which allow an instant release of the active agent upon sublingual administration, so that such formulation technology may be applied to buprenorphine and optionally opioid antagonists preferably being naloxone.

In a further embodiment, the present invention relates to the use of any of the aforementioned described pharmaceutical dosage forms comprising buprenorphine and optionally an opioid antagonist being preferably naloxone for the manufacture of a medicament for drug substitution therapy. The pharmaceutical dosage forms described above may, of course, also be used in the manufacture of a medicament for treating pain. Thus, the dosage forms may be used in opioid naïve patients or patients who are not dependent on opioids in order to provide fast pain relief by oral, preferably sublingual, administration of the preparations.

As far as drug substitution therapy is concerned, the effectiveness of the afore-described amounts and pharmacokinetic parameters of buprenorphine and optionally naloxone are known from the pharmaceutical preparations Subutex® and Suboxone®. Therefore it can be firmly assumed that the same efficacy will be observed in drug substitution therapy with the inventive preparations of the present invention.

One of the advantages of the preparations in accordance with the present invention is to be seen in the fact that in view of the instant release of buprenorphine, a drug addict will have a diminished chance of illicitly diverting the dosage form given that particularly the film-type and the wafer-type of dosage forms will disintegrate instantly upon contact with the saliva during sublingual administration. If an opioid antagonist such as naloxone is included in the dosage form it is additionally ensured that parenteral abuse of such dosage forms by dissolving the active agents out of the rapidly disintegrating dosage forms will be significantly diminished.

In yet a further embodiment, the present invention relates to a method of drug substitution therapy in drug addicts by administering a pharmaceutical formulation as described above which instantly releases buprenorphine and optionally an opioid antagonist being preferably naloxone upon oral, preferably sublingual, administration to a patient.

One embodiment of the present invention also relates to a method of treating pain by administering a pharmaceutical formulation as described above which instantly releases buprenorphine and optionally an opioid antagonist being preferably naloxone upon oral, preferably sublingual, administration to a patient.

The present invention has been described by reference to some of its preferred embodiments. This description is, however, in no way meant to limit the scope of the invention. Other embodiments that do not depart from the spirit of the invention should be similarly encompassed and addressed by the aforementioned description and the subsequent claims.

The invention claimed is:

1. A sublingual pharmaceutical dosage form, comprising:
approximately 0.1 mg to approximately 16 mg buprenorphine or an equivalent amount of a pharmaceutically acceptable salt thereof;
naloxone or a pharmaceutically acceptable salt thereof; and
at least one non-gelatin polymeric film-forming material;
wherein the buprenorphine or the equivalent amount of the pharmaceutically acceptable salt thereof and naloxone or the pharmaceutically acceptable salt thereof are in a weight ratio of from 1:1 to 10:1;
wherein the dosage form is in the form of a film and wherein the buprenorphine or the equivalent amount of the pharmaceutically acceptable salt thereof and the naloxone or the pharmaceutically acceptable salt thereof are dissolved or homogeneously dispersed in the film;
wherein the dosage form releases substantially all of the buprenorphine or the pharmaceutically acceptable salt thereof and the naloxone or the pharmaceutically acceptable salt thereof within less than 5 minutes after sublingual administration of the dosage form such that approximately substantially all of the buprenorphine and naloxone or the pharmaceutically acceptable salts thereof are absorbed by the sublingual mucosa; and
wherein the dosage form achieves:
(i) an average buprenorphine $AUC_{0-48}$ from approximately 10 to approximately 15 (hrs*ng)/ml when 4 mg buprenorphine or an equivalent amount of a pharmaceutically acceptable salt thereof is administered sublingually,
(ii) an average buprenorphine $AUC_{0-48}$ from approximately 15 to approximately 25 (hrs*ng)/ml when 8 mg buprenorphine or an equivalent amount of a pharmaceutically acceptable salt thereof is administered sublingually, or
(iii) an average buprenorphine $AUC_{0-48}$ from approximately 25 to approximately 40 (hrs*ng)/ml when 16 mg buprenorphine or an equivalent amount of a pharmaceutically acceptable salt thereof is administered sublingually.

2. The sublingual pharmaceutical dosage form according to claim 1, wherein the dosage form achieves:
(i) an average buprenorphine $C_{max}$ from approximately 1.5 ng/ml to approximately 2.25 ng/ml when 4 mg buprenorphine or an equivalent amount of a pharmaceutically acceptable salt thereof is administered sublingually,
(ii) an average buprenorphine $C_{max}$ from approximately 2.5 ng/ml to approximately 3.5 ng/ml when 8 mg buprenorphine or an equivalent amount of a pharmaceutically acceptable salt thereof is administered sublingually, or
(iii) an average buprenorphine $C_{max}$ from approximately 5.5 ng/ml to approximately 6.5 ng/ml when 16 mg buprenorphine or an equivalent amount of a pharmaceutically acceptable salt thereof is administered sublingually.

3. The sublingual pharmaceutical dosage form according to claim 1, wherein said dosage form comprises approximately 2 mg to approximately 8 mg buprenorphine or the equivalent amounts of a pharmaceutically salt thereof.

4. The sublingual pharmaceutical dosage form of claim 1, wherein said dosage form comprises buprenorphine or the equivalent amount of the pharmaceutically acceptable salt thereof and naloxone or a pharmaceutically acceptable salt thereof in a weight ratio of 2:1 to 8:1.

5. The sublingual pharmaceutical dosage form according to claim 4, wherein said dosage form comprises buprenorphine or the equivalent amount of the pharmaceutically acceptable salt thereof and naloxone or the pharmaceutically acceptable salt thereof in a weight ratio of 4:1.

6. The sublingual pharmaceutical dosage form according claim 1, wherein an average $T_{max}$ from approximately 45 to approximately 90 minutes is obtained after administration.

7. The sublingual pharmaceutical dosage form of claim 1, wherein the dosage form comprises the equivalent amount of buprenorphine hydrochloride.

8. The sublingual pharmaceutical dosage form according to claim 1, wherein the dosage form achieves an average buprenorphine $AUC_{0-48}$ from approximately 10 to approximately 15 (hrs*ng)/ml when 4 mg buprenorphine or an equivalent amount of a pharmaceutically acceptable salt thereof is administered sublingually.

9. The sublingual pharmaceutical dosage form according to claim 1, wherein the dosage form achieves an average buprenorphine $AUC_{0-48}$ from approximately 15 to approximately 25 (hrs*ng)/ml when 8 mg buprenorphine or an equivalent amount of a pharmaceutically acceptable salt thereof is administered sublingually.

10. The sublingual pharmaceutical dosage form according to claim 1, wherein the dosage form achieves an average buprenorphine $C_{max}$ from approximately 1.5 ng/ml to approximately 2.25 ng/ml when 4 mg buprenorphine or an equivalent amount of a pharmaceutically acceptable salt thereof is administered sublingually.

11. The sublingual pharmaceutical dosage form according to claim 1, wherein the dosage form achieves an average buprenorphine $C_{max}$ from approximately 2.5 ng/ml to approximately 3.5 ng/ml when 8 mg buprenorphine or an equivalent amount of a pharmaceutically acceptable salt thereof is administered sublingually.

12. The sublingual pharmaceutical dosage form according to claim 1, further comprising a pH modifier.

13. The sublingual pharmaceutical dosage form according to claim 12, wherein the pH modifier is selected from the group consisting of citric acid, tartaric acid, phosphoric acid, hydrochloric acid, and maleic acid.

14. The sublingual pharmaceutical dosage form according to claim 1, wherein the film is mucoadhesive.

\* \* \* \* \*